(12) United States Patent
Spitzer

(10) Patent No.: US 6,863,669 B2
(45) Date of Patent: Mar. 8, 2005

(54) DOUBLE IRRIGATING BIPOLAR SURGERY FORCEPS

(76) Inventor: Daniel E. Spitzer, 850 Piermont Ave., Piermont, NY (US) 10968

( * ) Notice: Subject to any disclaimer, the term of this patent is extended or adjusted under 35 U.S.C. 154(b) by 0 days.

(21) Appl. No.: 10/349,646

(22) Filed: Jan. 23, 2003

(65) Prior Publication Data

US 2003/0139743 A1 Jul. 24, 2003

Related U.S. Application Data

(60) Provisional application No. 60/365,729, filed on Mar. 19, 2002, and provisional application No. 60/352,002, filed on Jan. 23, 2002.

(51) Int. Cl.[7] .............................................. A61B 18/18
(52) U.S. Cl. ........................................ 606/51; 606/205
(58) Field of Search .............................. 606/39–42, 45, 606/46, 48, 49, 50–52

(56) References Cited

U.S. PATENT DOCUMENTS 5,295,956 A * 3/1994 Bales et al. .................... 606/49
6,096,037 A * 8/2000 Mulier et al. ................. 606/49

* cited by examiner

*Primary Examiner*—Rosialnd Rollins
(74) *Attorney, Agent, or Firm*—Cohen, Pontani, Lieberman & Pavane

(57) ABSTRACT

A double irrigating bipolar surgery forceps for reducing char buildup on working regions of the forceps. Each of the two forceps arms provides electrical current to the working regions and carries a fluid conduit for delivering irrigating fluid to the working region of the arm. The fluid conduits are, in a preferred form of the invention, carried on an outside surface of each arm and deliver irrigating fluid to an inside surface of each arm proximate to or within the working region. In a particularly preferred embodiment, an open channel is formed on the inside surface of each working region and in communication with the distal end of the arm's fluid conduit for improved delivery of irrigating fluid from the fluid conduit onto the working region and to the cautery site.

14 Claims, 1 Drawing Sheet

DOUBLE IRRIGATING BIPOLAR SURGERY FORCEPS

RELATED APPLICATIONS

This application claims priority from U.S. Provisional Patent Application Ser. No. 60/352,002 which was filed on Jan. 23, 2002 and from U.S. Provisional Patent Application Ser. No. 60/365,729 which was filed on Mar. 19, 2002.

BACKGROUND OF THE INVENTION

1. Field of the Invention

This invention pertains to instruments used for surgical procedures. More particularly, the present invention is directed to improved bipolar surgery forceps having irrigated tips.

2. Description of the Related Art

Bipolar Cautery Electro-Mechanical Instruments ("bipolar instruments") have many uses in modern surgical practice including dissection and hemostatis and the like. The basic structure of these bipolar surgical instruments includes two elongated members or arms that are connected at one, i.e. the proximal, end of the members. The members are coupled to an alternating current power source for supplying an electrical potential across the conductive tips which are defined at the other (i.e. distal) ends of the members. In operation, these bipolar instruments pass a high frequency AC electrical current between the conductive tips which are placed into contact with patient tissue or vessels. Each tip of the bipolar instrument alternately functions as an active and a ground electrode to provide a more accurate transfer and delivery, to the tissue, of electrical energy than that attainable using Monopolar Electro-Mechanical Instruments.

Early versions of bipolar instruments were powered by spark-gap type electrical generators but exhibited poor cautery of animal tissue, as for example human tissue. Dr. Leonard Malis subsequently developed an improved pulse generator (the current commercial model of which is the CMC II, manufactured by Codman Surgical Products of Raynahm, Mass.) and various types of bipolar tips that have notably improved tissue cautery using bipolar instruments.

To assure electrical communication and contact between the tips of the bipolar instrument and the living tissue, and to also cool the instrument tips, a medical assistant would typically drip a saline-containing fluid onto the site of the surgery during the cautery procedure. Even so, the heat generated at the tip of the bipolar instrument and the effect of the electric current applied directly to the patient's tissue would convert blood on and in contact with the bipolar instrument tips into a "char" formed of heated proteins, and this char would collect on the instrument tips. The accumulated char would cause the tips(s) of the instrument to stick or adhere to the tissue being cauterized, which can prove disastrous if the tissue is (for example) a delicate and vital blood vessel. The char accumulating on the tips also increased the resistance to the flow of electrical current, thereby reducing the operating effectiveness of the bipolar instrument.

To counter the effects of accumulating char, a surgeon using such prior art bipolar instruments would need to periodically halt the cautery procedure and hand the bipolar instrument to an assisting or scrub nurse for cleaning of the instrument tips on a fairly frequent basis, typically as much as once or more each minute. Later and current bipolar instruments have sought to avoid this requirement for frequent cleaning of the tips by incorporating an irrigation tube mounted to or otherwise defined along one of the two elongated members for directly delivering irrigation fluid to the distal tip of that member or arm through the tube. With the irrigation tube connected to a pump, a surgeon controlling the pump is then capable of providing a more precise flow of irrigation fluid to the tissue. This frees up the scrub nurse who could then provide more meaningful assistance to the surgeon performing the cautery procedure. More importantly, the provision of a constant, controlled flow of irrigation fluid to one of the instrument tips markedly diminished the accumulation of char on the instrument, thus facilitating the performance of the surgery by lessening, although not eliminating, the need to regularly halt the surgical or cautery procedure for cleaning of the instrument tips by an assisting nurse. As a consequence, depending on the particular tissue being cauterized and the degree of electrical energy or power being delivered via this improved bipolar instrument, the distal tips would now need to be cleaned only every 3 to 5 minutes during a surgical procedure.

Accordingly, there is a need for a bipolar surgery forceps which can further reduce the build up of char on the forceps ends, thereby requiring less frequent tip cleaning than is required in heretofore known forceps.

SUMMARY OF THE INVENTION

The present invention provides improved irrigating bipolar surgery forceps which reduce the amount of char buildup on the working regions of the forceps, thereby allowing for extended duration of use of the improved forceps during a surgical procedure between forceps cleaning. In accordance with a preferred embodiment, the forceps have two elongated arms joined at one end to a base which provides voltage and irrigation fluid to the arms and, specifically, to the working regions of both arms located at the distal arm ends. The irrigation fluid is provided to the distal arm ends through separate fluid conduits supported by each arm which extend from proximate the base to proximate the distal arm ends. Each conduit includes a fluid conduit outlet for delivering the fluid to the working region.

In one embodiment, each fluid conduit outlet is angled with respect to each forceps arm to provide desired delivery of fluid to the working region.

In another embodiment, the fluid conduit outlet is in communication with a channel or notch formed at each distal end of each forceps arm, with the notch extending into the working region of each arm for improving fluid delivery to the working region.

In yet another embodiment, the fluid conduits are positioned on an outer surface of each arm so as to not interfere with a surgeon's line of sight along the length of the forceps to the cautery site.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures described herein.

BRIEF DESCRIPTION OF THE DRAWINGS

In the drawings, wherein like reference numerals denote similar elements throughout the several views.

DETAILED DESCRIPTION OF THE PRESENTLY PREFERRED EMBODIMENTS

Figure 3:
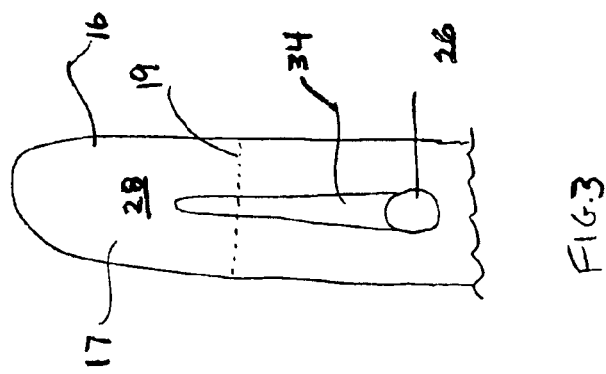
FIG. 3 is an enlarged plan view of the inner surface of the working region at the distal end of one of the forceps arms.
Figure 1:
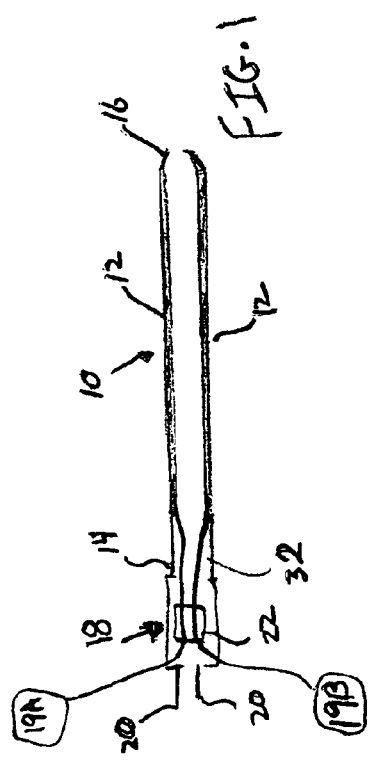
FIG. 1 is a side view of a forceps constructed in accordance with the present invention.
Figure 2:
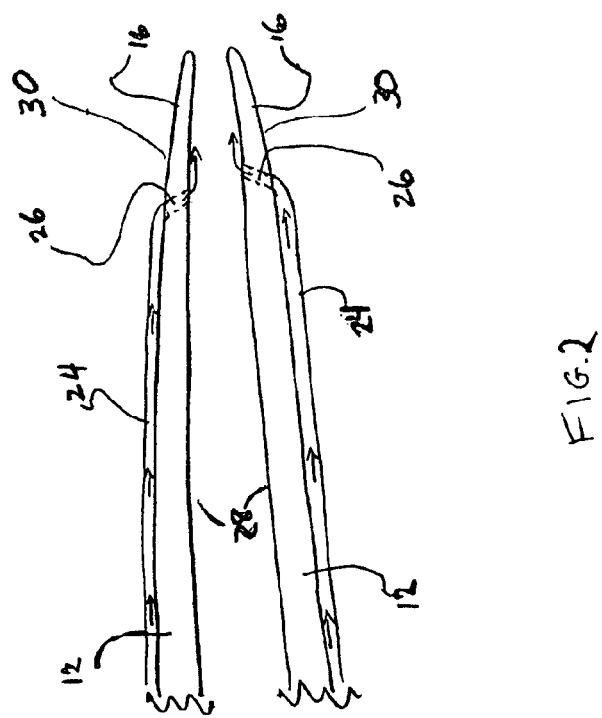
FIG. 2 is an enlarged view, of the distal ends of the forceps arms.

A double irrigating bipolar surgery forceps instrument 10 of the present invention as depicted by way of preferred embodiment in FIGS. 1–3 generally includes a pair of elongated members or arms 12 with each arm having a base end 14 and a distal end or tip 16. The base ends 14 are joined at or otherwise affixed to a base 18 fitted with or connected to a pair of electrodes 20 for providing electrical current along the arms 12 to the tips 16 in a manner well known to those of ordinary skill in the art.

In the bipolar instrument or forceps 10 of the present invention, each elongated member or arm 12 includes or carries a separate and independent irrigation fluid tube or conduit 24 that is fed from a separate supply of fluid 19A and 19B provided by a bifurcated fluid inlet 22 or functionally equivalent inlets positioned at the base 18 for irrigation of the respective distal end tip 16 of the member or arm. Thus, the inventive instrument uses two mechanically and electrically independent irrigation systems. Each irrigation system comprises a tube or conduit 24 carried on or defined integral with each elongated member 12 for delivering irrigation fluid from a supply of fluid to the distal tip 16 of that member. In use, both tips of the inventive bipolar instrument are thereby separately and independently irrigated as AC electrical current from voltage applied to electrodes 20 is supplied to and flows between the instrument tips 16 through the patient's tissue that is being cauterized. It is most important that the two supplies of irrigation fluid be isolated from each other in supplies 19A and 19B and through the respective fluid feed tubes to avoid shorting, through a common irrigation fluid supply, of the electric current that is intended to operatively flow between the tips, since the irrigation fluid must itself be electrically conductive to facilitate electrical contact and current flow from the tips to the tissue and between the bipolar tips via the tissue to be cauterized.

The bipolar instrument 10 of the invention may be implemented in any of a variety of contemplated ways and forms. For example, fluid can be pumped through the fluid conduits 24 either intermittently or continuously, using a peristaltic pump, a pulsatile pump, or via gravity feed (not shown), all of which are well known in the art. The irrigation fluid delivery conduits can be variously located or defined on and along the elongated members or arms, or otherwise on the forceps, as for example along the inner surface portions 28 of the arms 12 or along the outer surface portions 30 of the arms (as shown in FIG. 2) or so that they wrap partially or fully (either once or repeatedly) around the peripheries of the arms, or they may be defined integrally within the arms as channels defined longitudinally within and along the arms. The conduits 24 can furthermore terminate (for delivery of irrigation fluid to the tips) immediately adjacent, or closely proximate, or otherwise at any desired or otherwise appropriate location relative to the tips or along the lengths of the members for delivery of fluid to the tips. In preferred forms of the instrument 10, the fluid delivery channels are in any event preferably so defined on or along or within the elongated members, and the irrigation fluid is delivered to the channels from the independent fluid supplies (as shown by the directional arrows in FIG. 2), in such a manner as to avoid interfering with the surgeon's line-of-sight longitudinally along the instrument or otherwise to the instrument's distal tips for ease of viewing of the cautery site.

When in use, the surgeon typically views the cautery site by sighting at least partly along the elongated instrument arms between the adjustably-separated distal tips 16. Accordingly, in the most preferred implementations of the inventive instrument the fluid delivery channels or conduits are located other than along the interior, confrontingly-opposed surfaces 28 of the elongated members or arms. It is also important that the fluid delivery arrangement maximize the certainty of delivery of the irrigation fluid along the distal tips to the working region portion 17 of each distal tip 16 and then the cautery site. An imaginary reference boundary line 19 has been illustrated in FIG. 3 to delineate the working region portion 17 which comes in contact with the cautery site.

In the preferred implementation of FIGS. 1–3, fluid delivery along each elongated member or arm of the instrument is effected through the conduit 24 located on or along the outer face 30 of each elongated arm 12. (Alternatively, each conduit may be located on or along a side edge of a respective elongated arm—i.e. along an elongated edge defined between the outer 30 and inner 28 faces of the arm—although this alternative is less preferred, or may extend through the interior of the arm.) In any event, each conduit may be attached to or integrally or unitarily formed on or with the respective arm, and may be constructed of any suitable material. In the embodiment of FIGS. 1–3 a throughbore 26 is defined in and through each arm, from the outer to the inner surface of the arm, closely proximate—and preferably just proximal of—the proximal edge or boundary of the respective distal tip through which electrical current is applied to the cautery site. Irrigation fluid delivered toward the distal tip through each conduit is communicated from the conduit, via the throughbore, to the inner or interior face 28 of the respective arm and, to facilitate such communication, the throughbore may be angled obliquely or downwardly (from the outer to the inner surface of the arm) toward the distal tip at a suitable angle as shown in FIG. 2.

In a preferred embodiment, a small open channel or notch 34 may also be machined or otherwise defined in the inner surface of, and extending longitudinally along, each arm from the throughbore opening 26 on the inner surface 28 of the arm to the working region 17 of the distal tip 16 to further conduct and assure delivery of the irrigation fluid onto the distal tip and cautery site. The open channel, which may for example be configured as a conical or frustoconical delivery notch, may distally terminate at any suitable location within the working region 17 of the tip (as shown in FIG. 3) to facilitate delivery of the irrigation fluid onto that portion of the tip that contacts the cautery site.

In some forms or embodiments of the invention the instrument may include or be utilized in conjunction with a two-lumen irrigation tube attached to a bipolar cord 32 that is coupled to a control system (not shown) located either locally or remote with respect to the bipolar instrument. The control system may be operable to provide a graduated and controlled release of fluid through the irrigation tubes 24 along the arms 12 to the distal tips 16 of the instrument.

In one currently preferred embodiment, the elongated members or arms 12 are approximately 10 inches long, although other lengths (and predetermined arm shapes and bends and curvatures other than the straight-line form shown in FIG. 1) may also be employed within the intended scope and contemplation of the invention.

Based on experimental use of the invention it has been determined that approximately 30 minutes of operating time can be saved by virtue of the lack of any need to periodically halt the surgery or cautery procedure while the instrument is removed from the operating field for cleaning. Such advantageous results have never before been achieved or attained using prior art bipolar instruments.

While there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same result are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A double irrigating bipolar surgery forceps for providing irrigation fluid to a cautery site of a subject, said forceps comprising:

a first elongated arm and a second elongated arm, each of said first and second arms having a proximal base end and a distal tip that defines a working region intended for contact with the cautery site;

a base connected to each of the first and second arms for joining said first and second arms at said arm base ends so as to form a forceps manipulatable by a user of the forceps for selectively adjusting a spacing between the distal ends of the first and second arms, said base providing electrical isolation between said first and second arms for delivery of a cauterizing current between the working regions of the first and second arms; and a first fluid conduit extending longitudinally along said first arm from said base end to proximate said distal tip of said first arm for delivery of irrigation fluid from a first irrigation fluid supply to said distal tip of said first arm through said first fluid conduit so as to deposit delivered fluid at the working region of said first arm, and a second fluid conduit extending longitudinally along said second arm from said base end to proximate said distal tip of said second arm for delivery of irrigation fluid from a second irrigation fluid supply to said distal tip of said second aim through said second fluid conduit so as to deposit delivered fluid at the working region of said second arm, and so am to irrigate the cautery site arid thereby reduce buildup of char on the working region of said first and second arms during use of said forceps through concurrent delivery of irrigation fluid to the working regions of both said first and second arms, the second irrigation fluid supply being independent of and electrically isolated from the first irrigation fluid supply.

2. A double irrigating bipolar surgery forceps in accordance with claim 1, wherein the fluid conduit on each of the first and second arms comprises a throughbore defined through said each arm from an outside surface to an inside surface of said each arm proximate the distal tip of said each arm, and a fluid delivery tube carried on the outside surface of said each arm and extending from the base end of said each arm to said throughbore of said each arm for delivery of irrigation fluid from the irrigation fluid supply to said throughbore and through said throughbore to the inside surface of said each arm to deposit delivered fluid onto the working region of said each arm.

3. A double irrigating bipolar surgery forceps in accordance with claim 2, wherein the fluid conduit on each of the first and second arms further comprises an open channel defined in the inside surface of said each arm and extending from at least proximate said throughbore to at least proximate said working region of said each arm for directing irrigating fluid delivered Through said throughbore of said each arm to the working region of said each arm to irrigate the cautery site.

4. A double irrigating bipolar surgery forceps in accordance with claim 3, wherein said open channel is configured as one of conical and frustoconical.

5. A double irrigating bipolar surgery forceps in accordance with claim 2, wherein said throughbore of said each arm is angled toward said distal tip of said each arm from said outside surface toward said inside surface of said each arm.

6. A double irrigating bipolar surgery forceps in accordance with claim 1, wherein the fluid conduit of said each arm is integrally formed with said each respective arm.

7. A double irrigating bipolar surgery forceps in accordance with claim 1, wherein the fluid conduits of said first and second arms define a two-lumen irrigation tube.

8. A double irrigating bipolar surgery forceps in accordance with claim 1, wherein the supply of irrigation fluid comprises first and second irrigation fluid supplies which are electrically isolated from each other.

9. A double irrigating bipolar surgery forceps in accordance with claim 3, wherein said channel and said throughbore on said each arm are formed by at least one of machining and molding.

10. A double irrigating bipolar surgery forceps for providing irrigation fluid to a working region of said forceps for irrigating a cautery site, comprising:

a first elongated arm and a second elongated arm, each of said first and second arms having a proximal base end and a distal tip that defines a working region intended for contact with the cautery site, with each arm having an outside surface, an inside surface and a distal tip, wherein the working region is defined on said inner surface proximate said distal tip of each arm, each arm having an open channel formed in said inside surface, each said open channel having an outlet extending into the working region of each distal tip, and an inlet, and each said arm defining a throughbore extending, for each arm, from said outside surface to said inside surface and in communication with said respective channel inlet;

a first fluid conduit extending along said first elongated arm, and a second fluid conduit extending along said second elongated arm, each fluid conduit having an outlet in communication with said channel inlet, and an inlet disposed at another end of each said arm; and a base connected to each of said arms for joining said arms at said proximal arm base ends so as to form a forceps manipulatable by a user of the forceps for selectively adjusting a spacing between the distal ends of the arms, said base providing electrical isolation between said arms for delivery of a cauterizing current between the working regions of the arms, said base having means for delivering cauterizing current to each said working regions, and having means for providing irrigation fluid to each fluid conduit inlet, so that irrigation fluid is directed through said fluid conduits along said outside surfaces of said arms and through said respective throughbores for irrigating said working regions of said forceps, wherein said means for providing irrigation fluid comprises a first and a second irrigation fluid supply, said first irrigation supply delivering fluid to the first fluid conduit, said second irrigation supply delivering fluid to die second fluid conduit, such that the first irrigation fluid supply is electrically isolated from the second irrigation fluid supply, thereby avoiding a shorting of electrical current through the irrigation fluid provided to said first and second fluid conduit inlets.

11. A double irrigating bipolar surgery forceps in accordance with claim 10, wherein said open channel is configured as one of conical and frustoconical.

12. A double irrigating bipolar surgery forceps in accordance with claim 10, wherein said throughbore of said each arm is angled toward said distal tip of said each arm from said outside surface toward said inside surface of said each arm.

13. The forceps of claim 10, wherein the fluid conduits of each arm is integrally formed with each said respective arm.

14. A double irrigating bipolar surgery forceps in accordance with claim 10, wherein the fluid conduits of said first and second arms define a two-lumen irrigation tube.

* * * * *